(12) United States Patent
Trigg et al.

(10) Patent No.: US 6,777,386 B2
(45) Date of Patent: Aug. 17, 2004

(54) SUSTAINED PEPTIDE-RELEASE FORMULATION

(75) Inventors: Timothy Elliot Trigg, Warrawee (AU); John Desmond Walsh, Curl Curl (AU); Paul Adam Schober, Beacon Hill (AU)

(73) Assignee: Peptech Limited, New South Wales (AU)

( * ) Notice: Subject to any disclaimer, the term of this patent is extended or adjusted under 35 U.S.C. 154(b) by 14 days.

(21) Appl. No.: 09/991,714

(22) Filed: Nov. 26, 2001

(65) Prior Publication Data

US 2002/0052320 A1 May 2, 2002

Related U.S. Application Data

(63) Continuation of application No. 09/242,635, filed on Feb. 19, 1999, now Pat. No. 6,337,318.

(30) Foreign Application Priority Data

| Aug. 30, 1996 | (AU) | PO2035 |
| Dec. 6, 1996 | (AU) | PO4107 |
| Sep. 1, 1997 | (WO) | PCT/AU97/00560 |

(51) Int. Cl.$^7$ ............................................. A61K 38/00
(52) U.S. Cl. ............................................. 514/2; 514/15
(58) Field of Search ....................... 514/2, 15; 424/484

(56) References Cited

U.S. PATENT DOCUMENTS

| 5,039,660 A | 8/1991 | Leonard | |
| 5,256,649 A | 10/1993 | LeFur et al. | |
| 5,340,585 A | 8/1994 | Pike | |
| 5,372,996 A | * 12/1994 | Labrie | 514/15 |
| 5,573,781 A | * 11/1996 | Brown et al. | 424/484 |
| 5,925,619 A | 7/1999 | Walsh | |
| 6,337,318 B1 | * 1/2002 | Trigg et al. | 514/15 |

FOREIGN PATENT DOCUMENTS

| AU | A-41059/85 | 10/1985 |
| EP | 0 158 277 | 10/1985 |
| EP | 0 254 693 | 1/1988 |
| GB | 2 052 258 | 1/1981 |
| WO | 86/04503 | 8/1986 |
| WO | 92/18107 | 10/1992 |
| WO | 93/15722 | 8/1993 |
| WO | 96/34012 | 10/1996 |

OTHER PUBLICATIONS

Hawley's Condensed Chemical Dictionary, 13$^{th}$ ed., John Wiley & Sons, Inc. pp. 666, 1046 and 1047 (1997).*
Liu et al, "Effects of Pituitary–Testicular Axis Suppression in Utero and during . . . ," Journal of Endocrinology and Metabolism, vol. 73, No. 5, pp. 1038–1043 (1991).
Hawley's Condensed Chemical Dictionary, 13$^{th}$ ed., John Wiley & Sons, Inc. pp. 666, 1046 and 1047 (1997).

* cited by examiner

Primary Examiner—Christopher R. Tate
Assistant Examiner—Maury Audet
(74) Attorney, Agent, or Firm—Nixon & Vanderhye

(57) ABSTRACT

A pharmaceutical and/or veterinary formulation for sustained release of a peptide agonist or analogue, comprising about 2–15% (w/w) of at least one peptide agonist or analogue other than deslorelin (on an active basis), about 0.5–3.5% (w/w) lecithin and the balance stearin. The formulation preferably comprises a GnRH agonist or analogue and is used for the treatment of various conditions where suppression of sex hormone levels is beneficial, particularly prostate cancer, ovarian and breast cancer, and benign prostatic hyperplasia in dogs.

5 Claims, 14 Drawing Sheets

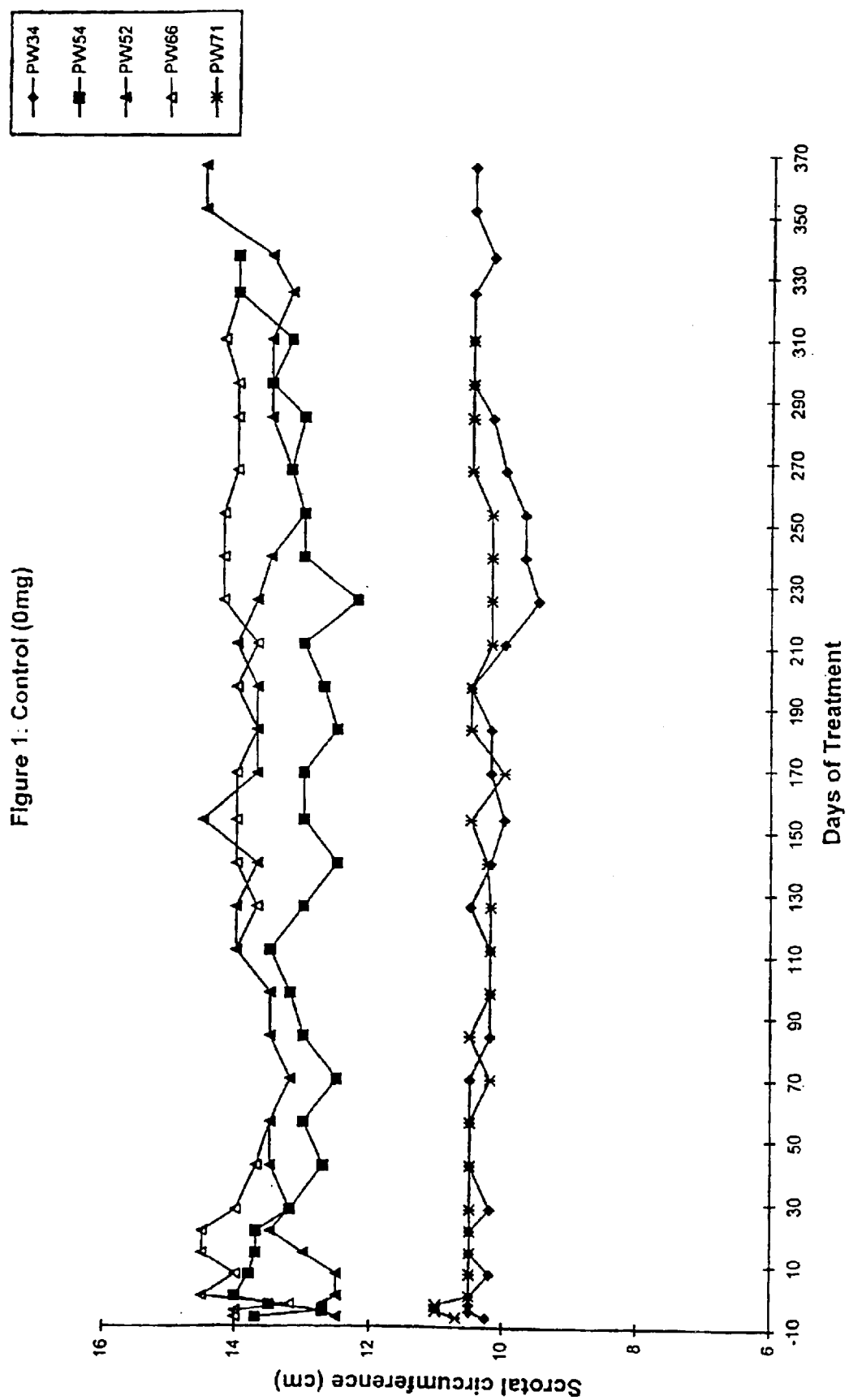
Figure 1: Control (0mg)

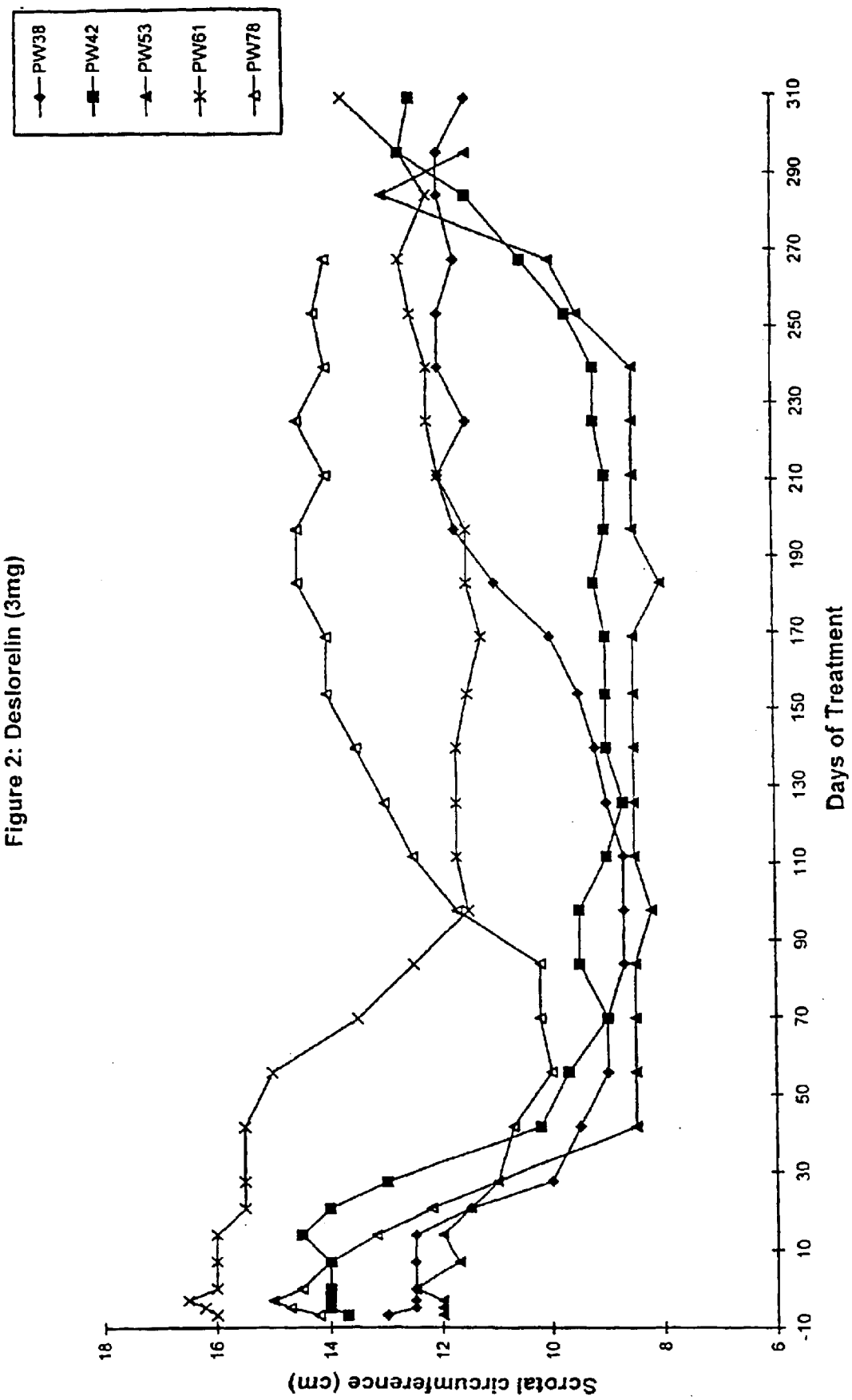

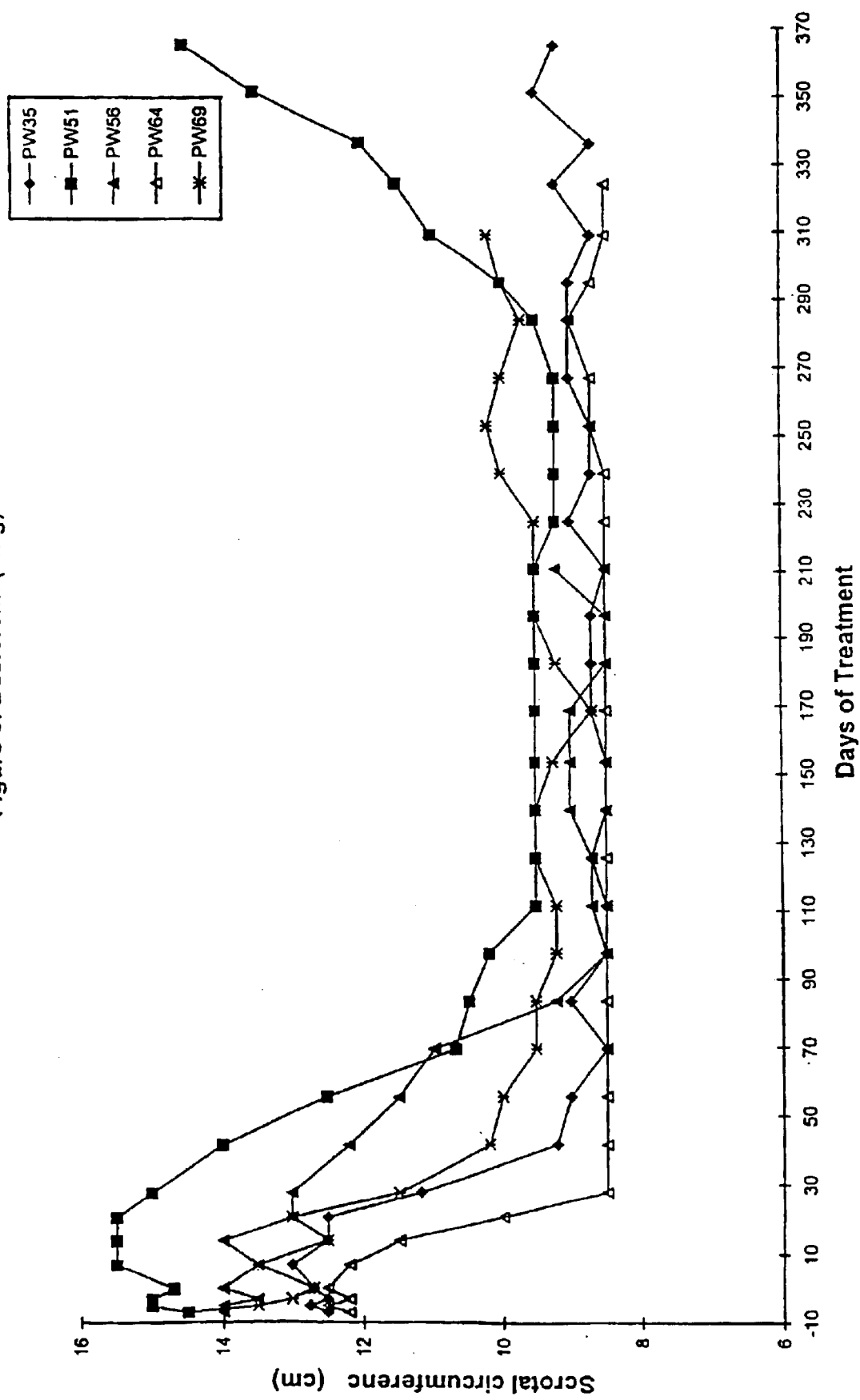

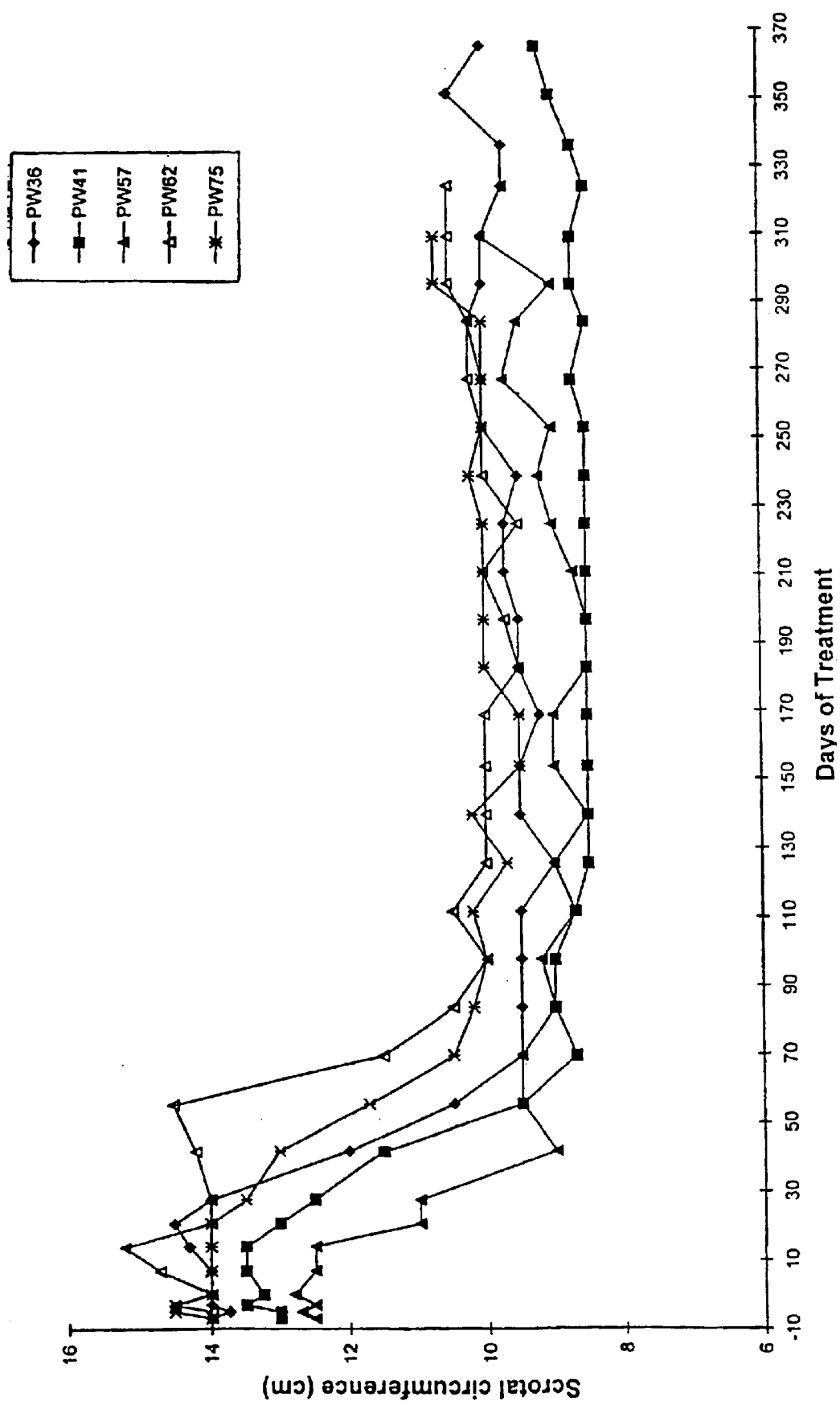
Figure 4: Deslorelin (12mg)

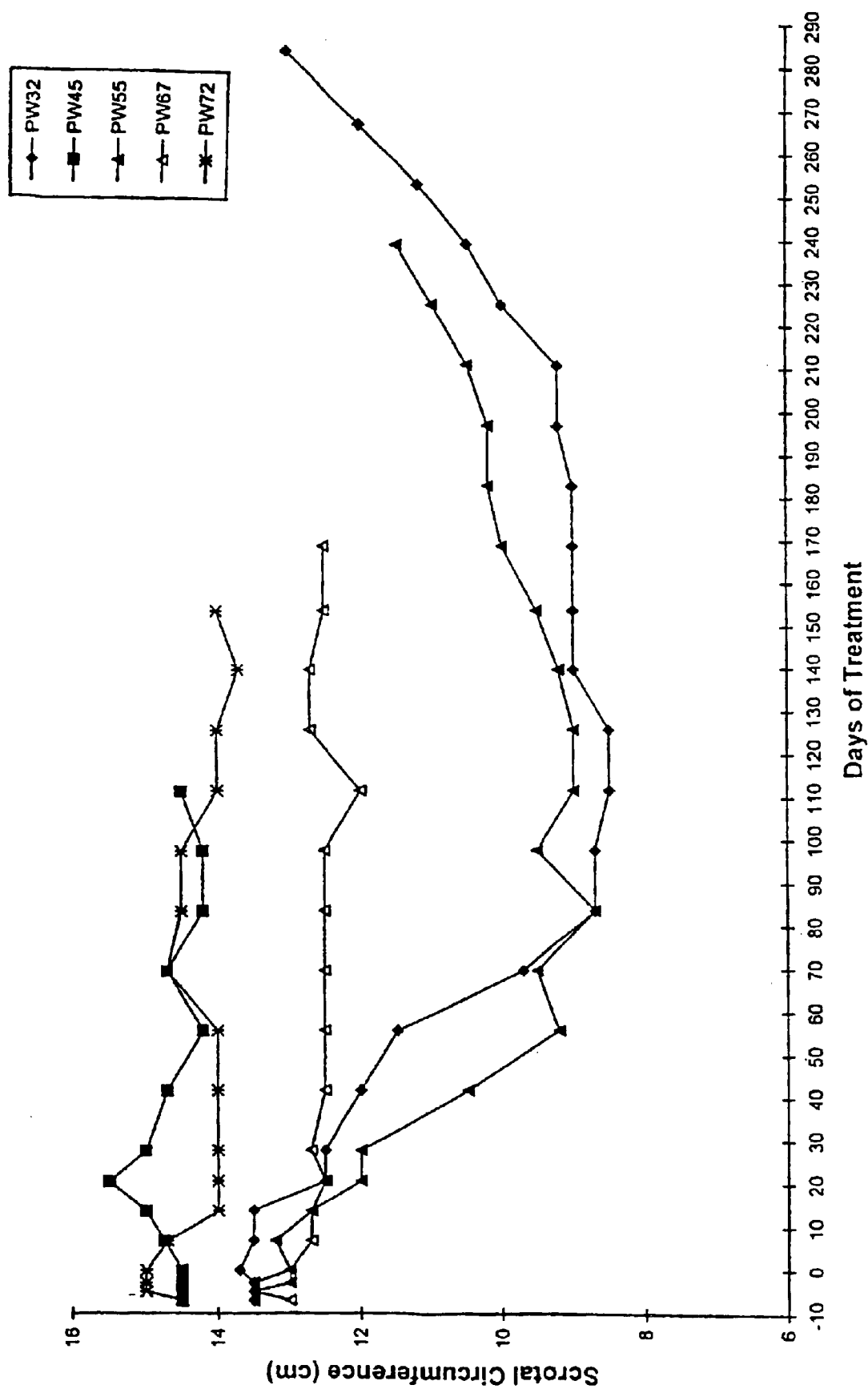

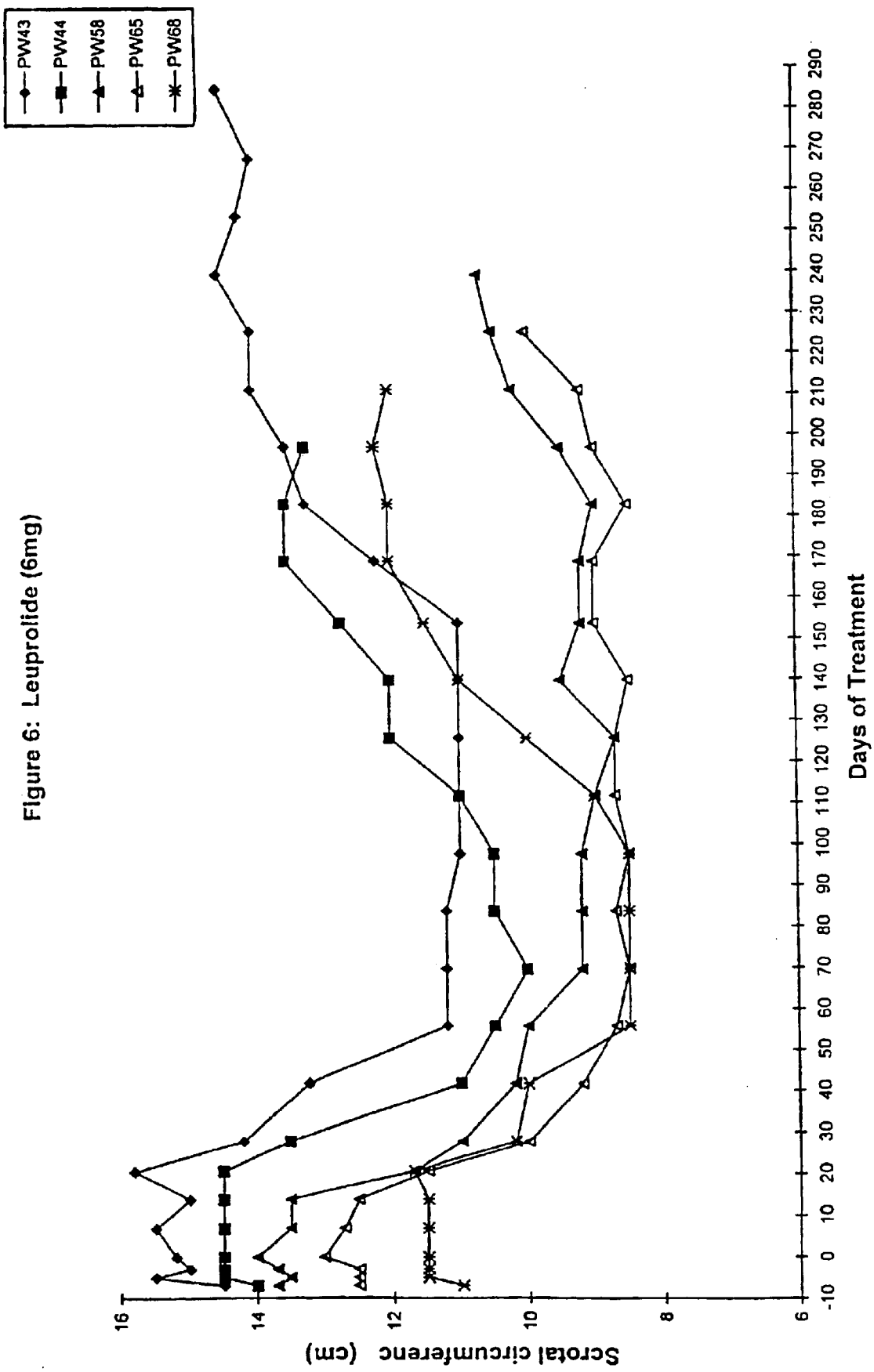

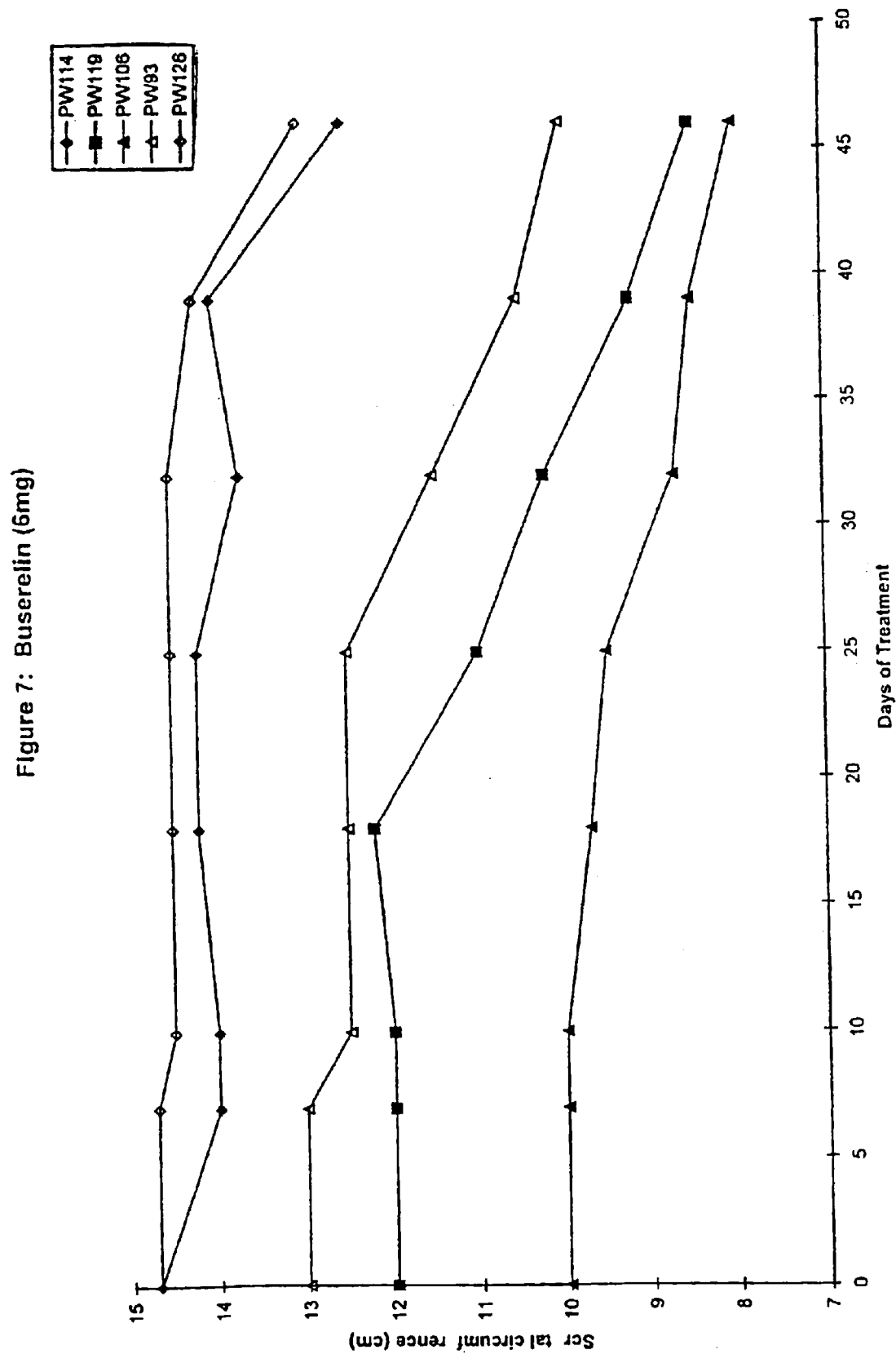

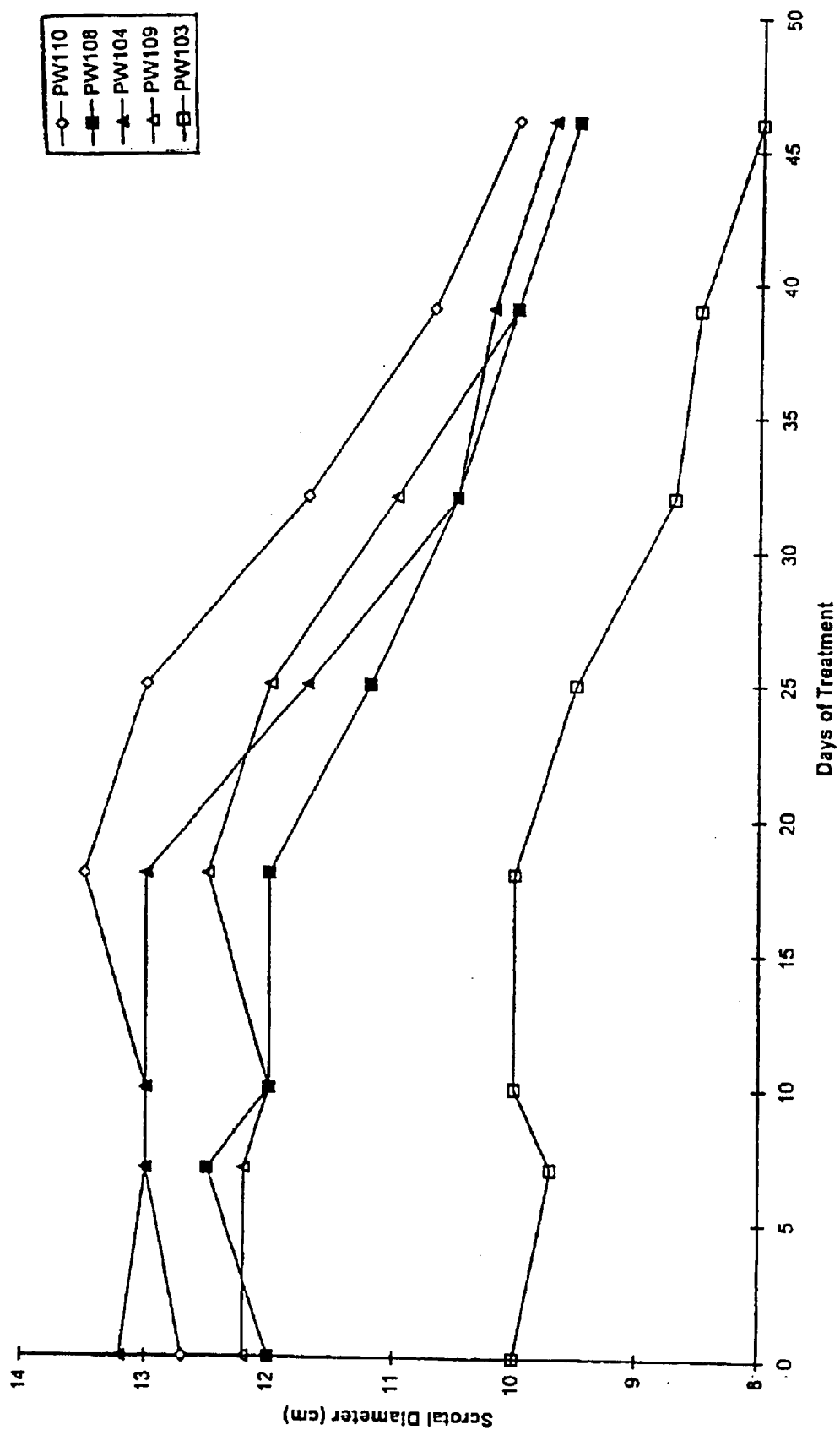
Figure 8 Triptorelin (6mg)

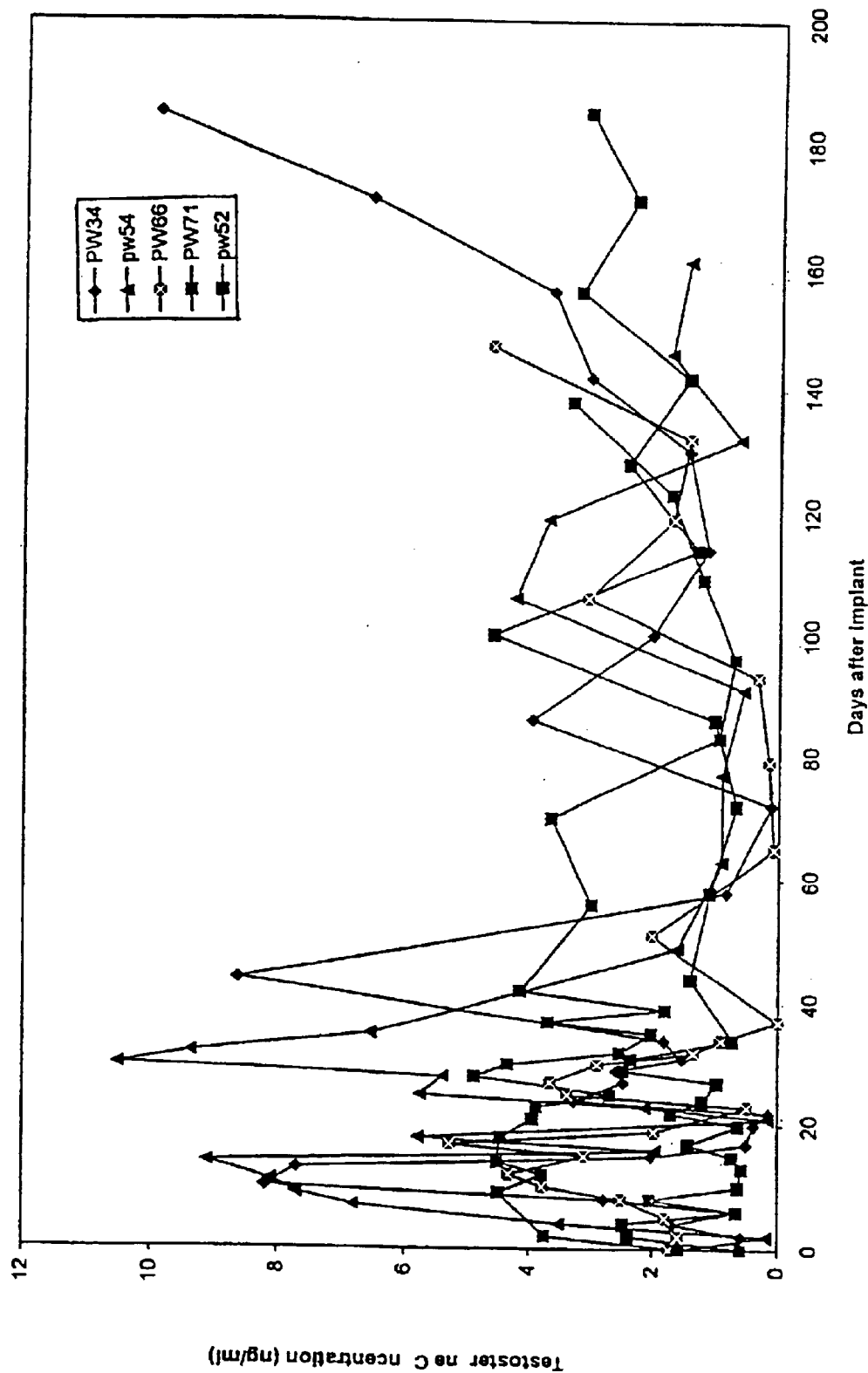

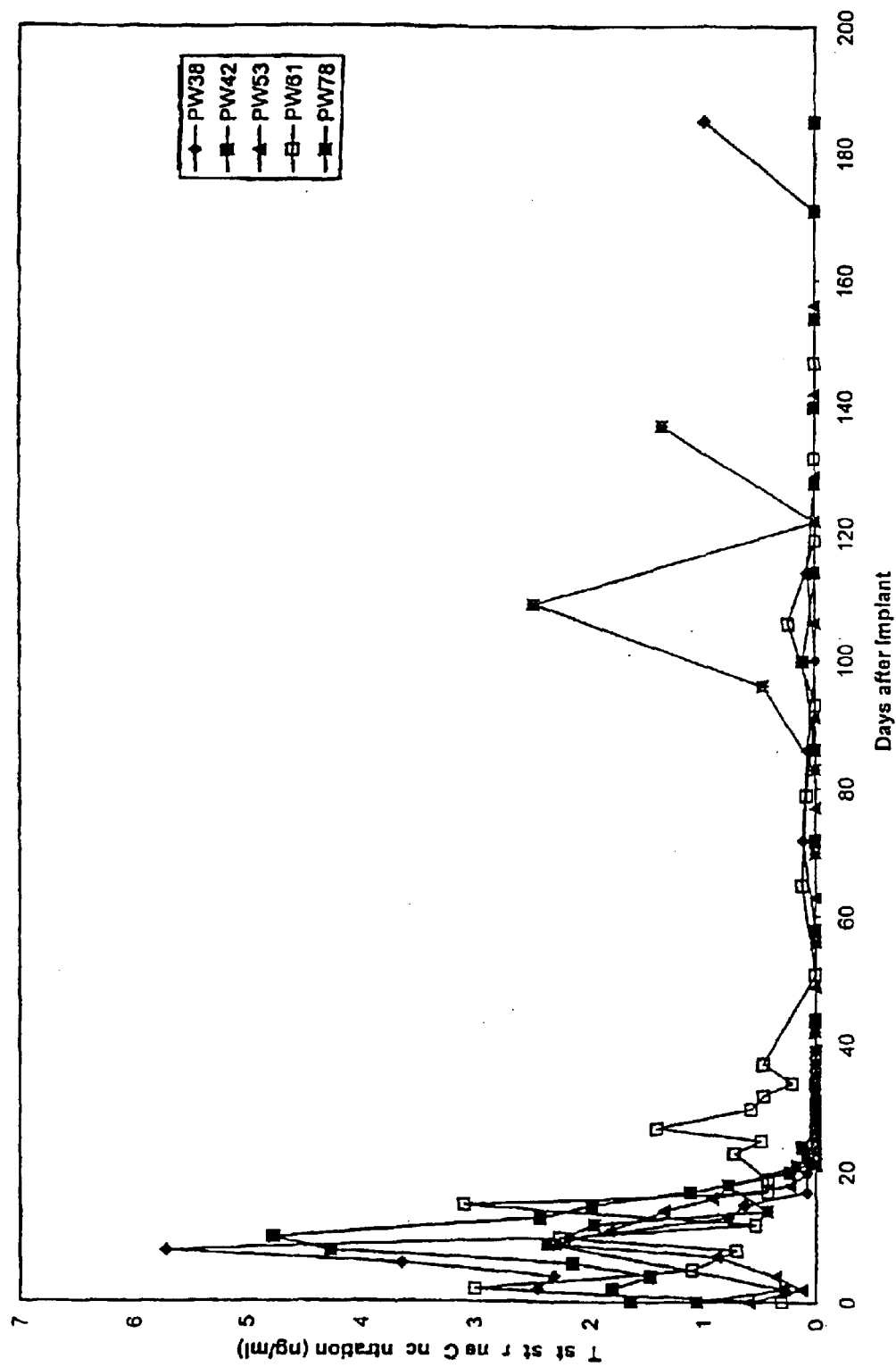

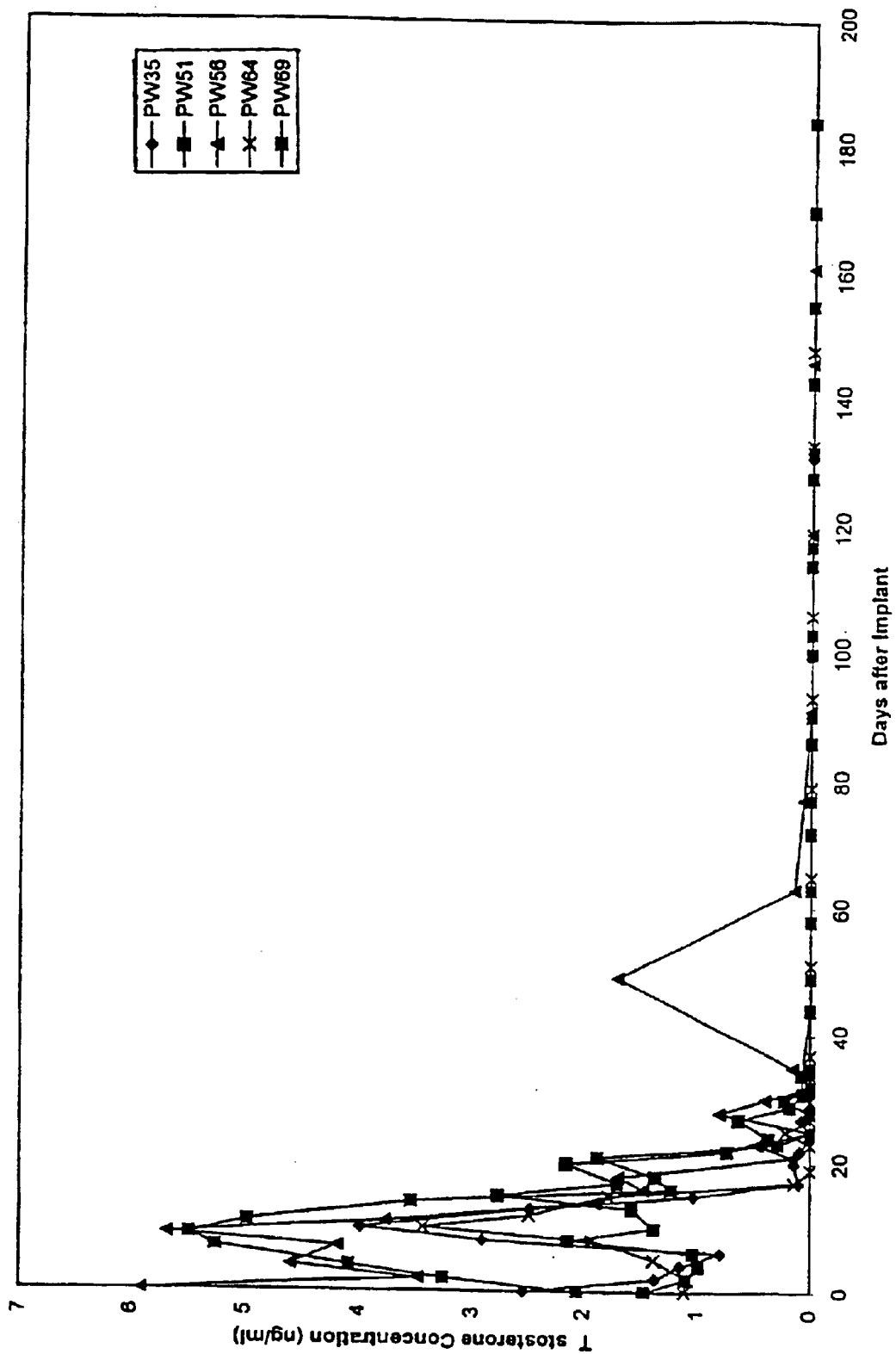

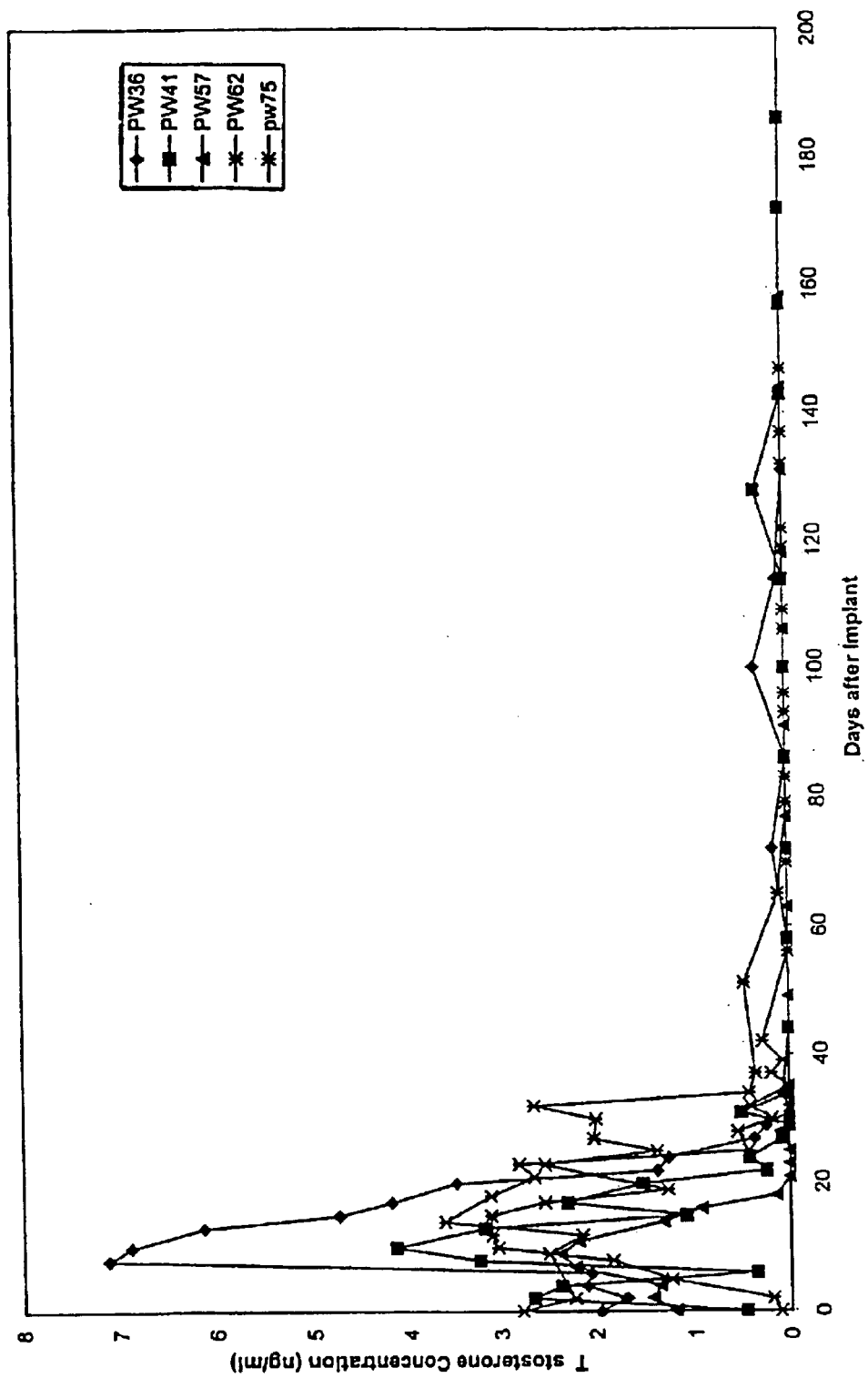
Figure 12: Plasma Testosterone Concentration Deslorelin (12mg)

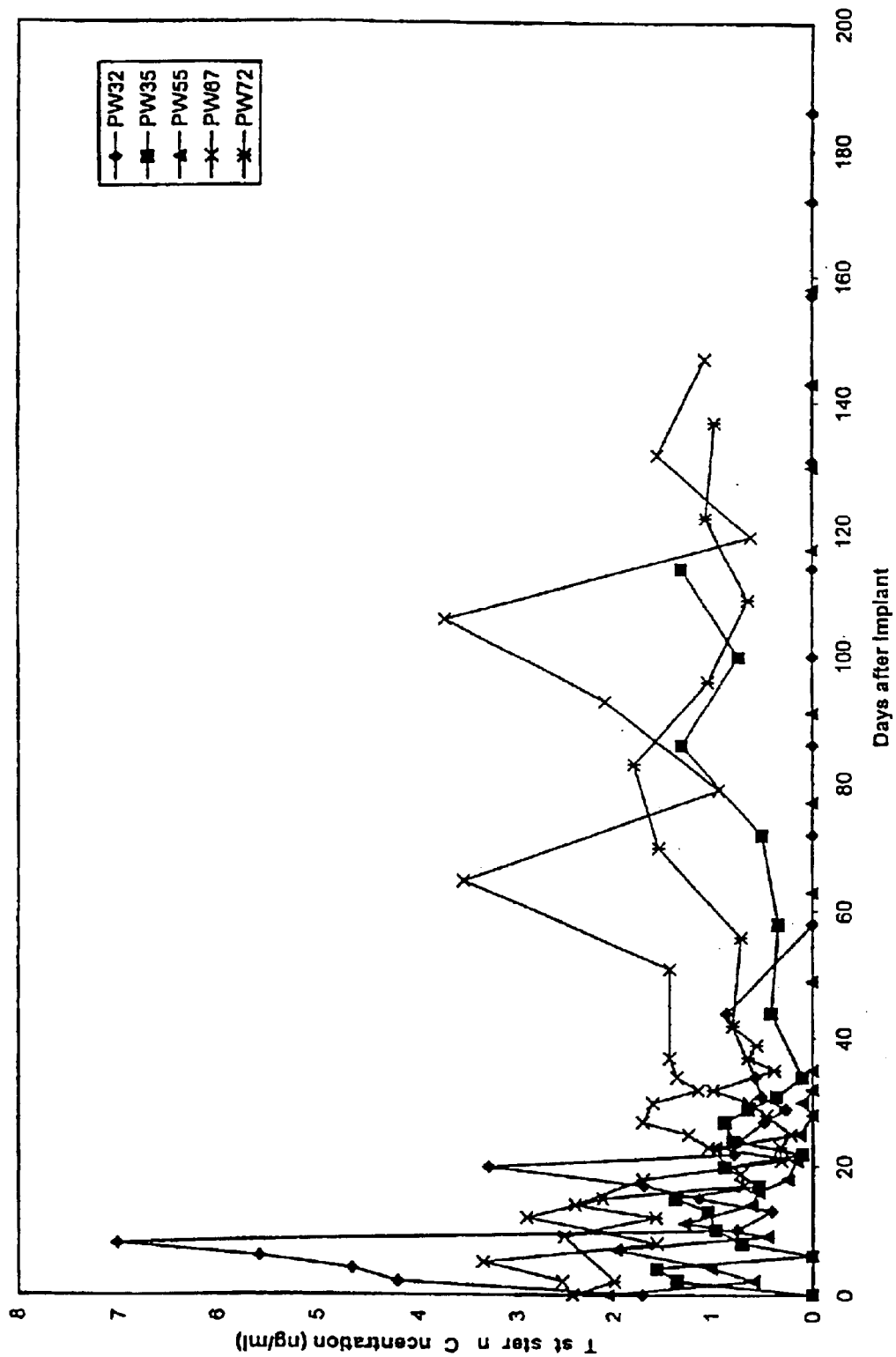

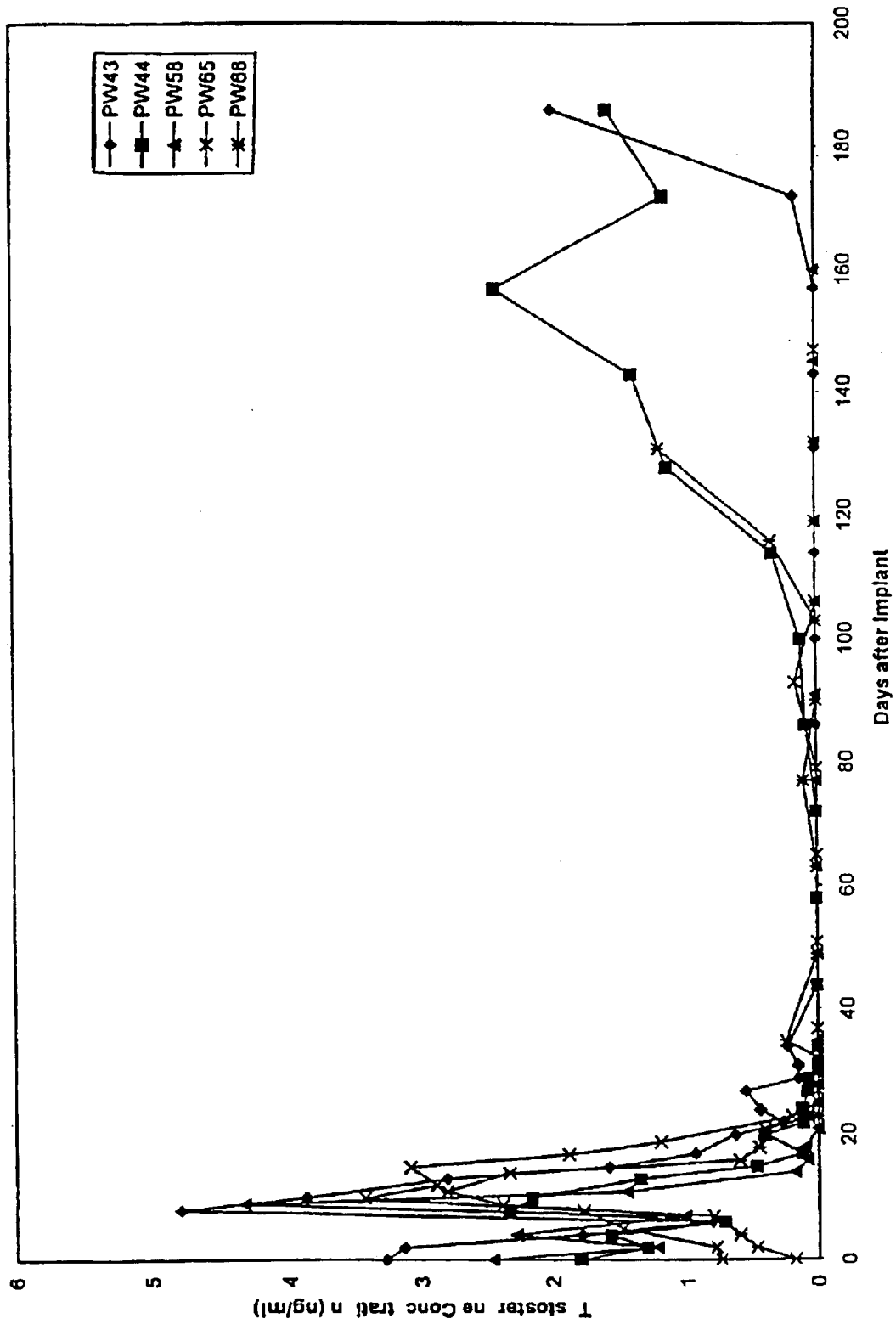
Figure 14: Plasma Testosterone Concentration Leuprolide (6mg)

SUSTAINED PEPTIDE-RELEASE FORMULATION

This application is a continuation of U.S. application Ser. No. 09/242,635, filed Feb. 19, 1999, now U.S. Pat. No. 6,337,318, which claims the benefit of PCT/AU97/00560, filed Sep. 1, 1997, the contents of which are hereby incorporated by reference in this application.

FIELD OF THE INVENTION

The present invention relates to formulations for the sustained release of peptide agonists and analogues. In a particular application of the invention, the formulation comprises a peptide agonist or analogue of gonadotropin releasing hormone (GnRH) and is used for the treatment of prostate and breast cancer and other diseases and conditions where suppression of testosterone or estradiol levels is beneficial.

BACKGROUND OF THE INVENTION

The peptide gonadotropin releasing hormone (GnRH) has been the subject of intensive research for many years. It is a hypothalamic decapeptide which is synthesised and stored in neurosecretory cells of the medial basal hypothalamus. The releasing hormone is released in a pulsatile manner into the hypophysial portal circulation and is transported to the anterior pituitary. Here, it regulates the secretion of the gonadotrophins, leuteinising hormone (LH) and follicle stimulating hormone (FSH), into the systemic circulation. Thus, GnRH is a humoral link between the neural and endocrine components of reproductive function (for review see Conn PM (ed) 1996 Gonadotropin-releasing hormone Endocrine Review 7:1). GnRH binds to a single class of receptors on gonadotrope cells. Prolonged exposure of these cells to the GnRH results in loss of responsiveness to the hormone, through receptor alteration (reviewed in Hazum E and Conn PM (1988) Endocrine Review 9:379–866). The outcome of down-regulation of responsiveness to GnRH is suppression of circulating levels of gonadotropins and sex hormones. This has the consequence of suppressing reproductive function and other processes affected by sex hormone levels.

In the present applicant's co-pending International Patent Application No PCT/AU96/00370 (the disclosure of which is incorporated herein by reference) there is described a formulation comprising deslorelin, a GnRH agonist, as the active agent which, when administered to animals, prevents reproductive function over an extended and predictable period of time. The formulation also allows the restoration of reproductive function following termination of administration. It is also disclosed that this formulation may be used in the treatment of prostate and breast cancer and other diseases or conditions where suppression of testosterone or estradiol levels is beneficial.

The use of GnRH agonists and analogues for the suppression of hormone levels in humans is well documented. Van Leusden HAIM (Gynecol Endocrinol 8 (1994) 215–222) has reviewed the use of a variety of GnRH agonist peptides for suppression of estradiol levels in female patients and use for the treatment of endometriosis and leiomyoma. From a survey of a large body of published work, these authors concluded that many GnRH analogues. including deslorelin, were effective in suppressing estradiol levels and hence in treating these sex hormone-accelerated conditions provided that the peptide was delivered so as to maintain a constant minimum blood level. The prerequisite for a peptide to be active was the ability to disturb the pulsatile release of endogenous GnRH. This required a constant minimum plasma level (this level was not defined). They suggested that a mode of delivery was more important than minor differences in potency between different GnRH analogues. These authors also concluded that in a suppressed pituitary, the dose of GnRH analogue needed to maintain suppression gradually decreased with the duration of treatment (also explored in Sandow J and Donnez T (1990) in Brosens I, Jacobs H S and Rennebaum B (eds) LHRH analogues in Gynaecology pp 17–31 Camforth: Parthenon Publishing).

The use of GnRH agonists or analogues for the treatment of various benign hormone-dependent diseases and conditions has been described. For example, Kappy M, et al. (J. Clin. Endocrinol. Metal. 64 (1987) 1320–1322) and Lee P A, et al. (J. Pediatr. 114 (1989) 321–324) describe the long-term treatment of precocious puberty in children using the GnRH agonist, leuprolide acetate. The use of this GnRH agonist in the treatment of hirsutism (Rittmaster R S & Thompson D L, J. Clin. Endocrinol. Metab. 70 (1990) 1096–1102) and endometriosis (Seltzer V L & Benjamin F, Obstet. Gynecol. 76 (1990) 929) has also been described. In addition, GnRH agonists or analogues may be used for treatments of uterine fibroids (Lumsden M A, et al., Lancet i (1987) 36–37; Healy D L, Gynecol. Endocrinol. 3 (suppl 2) (1989) 33–49), cyclic auditory dysfunction (Andreyko J L & Jaffe R B, Obstet. Gynecol. 74 (1989) 506), porphyria (Bargetzi M J et al., JAMA 261 (1989) 864) and benign prostatic hypertrophy (Gabrilove J L et al., J. Clin. Endocrinol. Metab. 69 (1989) 629).

Similarly, the use of GnRH agonists or analogues in the treatment of sex hormone dependent tumours, including breast cancer and prostate cancer, has been described. For example, de Voogt H J et al. (Scand. J. Urol. Nephrol. Suppl. 138 (1991) 131–136) describes the results obtained in a ten-year study of prostatic cancer patients administered buserelin, and Vogelzang N J et al. (Urology 46 (1995) 220–226) describes the use of monthly subcutaneous injections of goserelin in the treatment of advanced prostatic cancer. The goserelin was found to be well tolerated and as effective as orchiectomy. Redding et al, (1984) Proc Natl Acad Sci USA 81 5845–5848 described the use of a GnRH analogue triptorelin for suppression of prostate cancer in rats and demonstrated that a microencapsulated form of the peptide, delivering a controlled dose over a 30 day period was more effective in suppressing serum testosterone levels and prostate tumour weight than daily subcutaneous administration of equivalent or double doses of the free peptide. The value of this analogue in human prostate cancer patients to suppress testosterone levels and show tumour progression has been demonstrated by Parmar H et al (1985) The Lancet Nov 30, 1201–1205. This one month depot injection of a GnRH agonist has now been registered for use and tested and used widely in the treatment of breast, ovarian and prostate cancer, endometriosis, myoma and in precocious puberty in children, as have other GnRH agonists (see Nelson J R and Corson S L (1993) Fertil Steril 59: 441–3; Paul D et al. (1995) J Clin Endocrin Metab 80: 546–551). A three month depot preparation of a GnRH agonist has also been described (Okada H et al. (1994) Pharm Res (US) 11: 1199–1203.). Linear drug release from the injected microspheres was obtained with persistent suppression of serum LH, FSH (rats) and testosterone (rats and dogs) for over 16 weeks. Doses of GnRH analogues used to suppress sex hormone levels in males and females are the same (e.g. Plosker, G L and Brogden, R V (1994) Drugs Vol. 48, pages 930–967). Thus, the demonstration of suppression of sex hormone levels in one sex is predictive of similar suppression in the other sex.

Accordingly, the abovementioned deslorelin formulation developed by the present applicant, is also useful for treating a range of hormone dependent diseases and conditions in animals (including humans) such as those mentioned above. The present applicant has now found that similar formulations including GnRH agonists or analogues other than deslorelin can also be used in treating a range of hormone dependent diseases and conditions in animals, including humans. However, these formulations offer an improved treatment for hormone dependent diseases and conditions, by continuing to deliver the GnRH agonist or analogue over a period of up to 12 months or more, thus reducing the need for frequent subcutaneous injections or implant insertions. Whilst formulations for sustained release of bioactive peptides (including GnRH and its agonists or analogues) for periods of up to 12 months have been previously proposed in U.S. Pat. No. 5,039,660, it is to be noted that the only release results provided in that specification relate to a formulation comprising GHRH placed in a bath of physiological, buffered saline for a period of merely twenty days.

DISCLOSURE OF THE INVENTION

Thus, in a first aspect, the present invention provides a pharmaceutical and/or veterinary formulation comprising about 2–15%(w/w) of at least one peptide agonist or analogue other than deslorelin (on an active basis), about 0.5–3.5% (w/w) lecithin and the balance stearin.

In a preferred embodiment of the present invention, the formulation comprises about 5–10% (w/w) peptide agonist or analogue other than deslorelin (on an active basis), about 0.5–1.5% (w/w) lecithin and about 89–94% (w/w) stearin.

Preferably, the peptide agonist or analogue is a GnRH agonist or analogue other than deslorelin. Particularly preferred formulations are;

(I) 94% (w/w) stearin, 5% (w/w) GnRH agonist or analogue other than deslorelin (on an active basis) and 1% (w/w) lecithin, and (II) 93% (w/w) stearin, 5% (w/w) GnRH agonist or analogue other than deslorelin (on an active basis) and 2% (w/w) lecithin.

In a still further preferred embodiment of the present invention the formulation is for administration to an animal selected from dogs, cats, other domestic animals, captive wildlife and humans.

Typically, the formulation of the first aspect will release the peptide agonist or analogue, in vitro, into phosphate buffered saline (PBS: pH 7.3, prepared by dissolving 8.00 g of sodium chloride, 1.00 g di-sodium hydrogen phosphate anhydrous, 0.40 g sodium dihydrogen phosphate dihydrate (0.31 g if anydrous), and 0.05 g sodium azide in 1 liter of deionised water), at 37° C. at a rate of about 2–350 $\mu$g/day for at least 200 days but preferably for at least 300 days.

The excipient(s) of stearin and lecithin is preferably in a non-crystalline form.

The formulation will typically exist in the form of rods which have been extruded. The rods may be cut into predetermined lengths for implantation in the animal. As will be readily appreciated, the length of rod will determine the rate and dose of the peptide agonist or analogue. As opposed to implanting longer rods more than one rod can be implanted in each animal.

Histopathological examinations conducted on dogs have shown, unexpectedly, that implanted rods of the formulation of the first aspect provoke only a minimal to mild inflammatory response resulting in the encapsulation of the rod or remnants within a thin layer of fibroblasts. While not wishing to be bound by theory, it is believed that the success of the formulation of the first aspect to continue to release the peptide agonist or analogue over periods of up to 12 months or more is due, at least in part, to the apparent ability of the formulation to be well tolerated in the animal body. The provocation of a stronger inflammatory response than that observed, could have been otherwise expected to result in the rod or remnants being heavily encapsulated by fibrous tissue thereby stifling release of the peptide agonist or analogue.

It will be appreciated by persons skilled in the art, that alternative formulations comprising excipient(s) with similar characteristics to those included in the formulation of the first aspect may likewise provoke minimal to mild inflammatory responses and consequently be useful for the sustained release of peptide agonists or analogues. Such alternative formulations are to be regarded as falling within the scope of the present invention.

In a second aspect, the present invention consists in a method of treating a disease or condition in an animal, the method comprising administering to the animal the formulation of the first aspect of the invention.

The disease or condition referred to in the method of the second aspect of the invention is, preferably, any disease or condition wherein reduction of sex hormone (testosterone or estradiol) levels over a prolonged period is beneficial. Examples include prostate cancer, ovarian and breast cancer, benign hormone-dependent disorders such as endometriosis, myoma and premenstrual tension, uterine fibroids, hirsutism, cyclic auditory dysfunction, porphyria and precocious puberty in children.

Persons skilled in the art will be well aware of a variety of GnRH agonists or analogues which can be usefully employed in the present invention. Examples of some of the GnRH agonists or analogues which may be used in the present invention include eulexin (described in FR7923545, WO 86/01105 and PT100899), goserelin (described in U.S. Pat. No. 4,100,274, U.S. Pat. No. 4,128,638. GB9112859 and GB9112825), leuprolide (described in U.S. Pat. No. 4,490,291, U.S. Pat. No. 3,972,859, U.S. Pat. No. 4,008,209, U.S. Pat. No. 4,005,063, DE2509783 and U.S. Pat. No. 4,992,421), dioxalan derivatives such as are described in EP 413209, triptorelin (described in U.S. Pat. No. 4,010,125, U.S. Pat. No. 4,018,726, U.S. Pat. No. 4,024,121, EP 364819 and U.S. Pat. No. 5,258,492), metereliin (described in EP 23904), buserelin (described in U.S. Pat. No. 4,003,884. U.S. Pat. No. 4,118,483 and U.S. Pat. No. 4,275,001), histrelin (described in EP217659), nafarelin (described in U.S. Pat. No. 4,234,571, WO93/15722 and EP52510), lutrelin (described in U.S. Pat. No. 4,089,946), leuprorelin (described in Plosker et al, Drugs 48 930–967, 1994) and LIIRH analogues such as are described in EP181236, U.S. Pat. No. 4,608,251, U.S. Pat. No. 4,656,247, U.S. Pat. No. 4,642,332, U.S. Pat. No. 4,010,149, U.S. Pat. No. 3,992,365 and U.S. Pat. No. 4,010,149. The disclosures of each the references referred to above are incorporated herein by cross reference.

Preferred GnRH agonists or analogues include goserelin, leuprorelin, triptorelin, meterelin, buserelin, histrelin, nafarelin and combinations thereof. The formula of these compounds is provided below:

Goserelin $C_{59}H_{84}N_{18}O_{14}C_2H_4O_2$ D-Ser(Bu$^t$)$^6$Azgly$^{10}$-LHRH Acetate 3-[5-oxo-L-prolyl-L-tryptophyl-L-seryl-L-tyrosyl-(3-O-tert-butyl)-D-seryl-L-leucyl-L-arginyl-L-prolyl]cabazamide acetate.

Leuprorelin $C_{59}H_{84}N_{16}O_{12}$, $C_2H_4O_2$ Leuprorelin Acetate 5-oxo-L-prolyl-L-histidyl-L-tryptophyl-L-seryl-L-tyrosyl-D-leucyl-L-arginyl-N-ethyl-L-prolinamide acetate.

Triptorelin $C_{59}H_{84}N_{16}O_{12}$, $C_2H_4O_2$ D-Trp$^6$-LHRH 5-oxo-L-prolyl-L-histidyl-L-tryptophyl-L-seryl-L-tyrosyl-D-tryptophyl-L-leucyl-L-arginyl-L-prolylglycinamide.

Meterelin Des Gly$^{10}$-2-methyl-D-Trp$^6$-Pro-ethyl-amide$^9$ LHRH.

Buserelin $C_{60}H_{86}N_{16}O_{13}$, $C_2H_4O_2$ D-Ser(Bu$^t$)$^6$-Pro9-NEt LHRH Acetate Oxo-L-prolyl-L-histidyl L-tryptophyl-L-seryl-L-tyrosyl-O-tert-butyl-D-seryl-L-leucyl-L-arginyl-N-ethyl-L-prolinamide acetate.

Histrelin Pro-His-Trp-Ser-Tyr-Leu-D(N-benzyl) His-Arg-Pro-N-ethylamide.

Nafarelin $C_{66}H_{83}N_{17}O_{13}$, $xC_2H_4O_2yH_2O$ Oxo-L-prolyl-L-histidyl-L-tryptophyl-L-seryl-L-tyrosyl-3-(2-naphthyl)-D-alanyl-L-leucyl-L-arginyl-N-ethyl-L-prolylglycinaminde acetate hydrate.

Stearin is partially hydrogenated palm oil. Its principle fatty acids are C16:0(45%) and C18:0(53%). Melting point is about 55° C.

Lecithin is a composition mainly comprised of phosphatidylcholine. It is a mixture of diglycerides of stearic, palmitic and oleic acids linked to the choline ester of phosphoric acid. Both stearin and lecithin are found in plants and animals.

In a third aspect, the present invention consists in a method of preventing reproductive function in an animal, the method comprising administering to the animal the formulation of the first aspect of the invention.

In addition, the formulation described in PCT/AU96/00370 comprising deslorelin as well as other similar formulations comprising other GnRH agonists and analogues, are also well suited for use in the treatment of benign prostatic hyperplasia, a condition which is common in dogs but uncommon to rare in other species.

Benign prostatic hyperplasia, which results from androgenic stimulation, is the most common prostatic disorder of dogs and is found in most intact male dogs aged >6 years old. The most common clinical signs are tenesmus, hematuria, bleeding from the penis and chronic recurrent infections of the urinary tract. These signs may be accompanied by nonspecific signs including fever, malaise and caudal abdominal pain—often present with bacterial neoplasia. In addition, prostatic diseases may cause infertility, incontinence or urethral obstruction.

The present treatment of choice for benign prostatic hyperplasia is castration. Following castration, prostatic involution is usually evident within a few weeks and is complete within a few months. For males intended for breeding, other treatments involving antiandrogens may be feasible. These drugs inhibit androgen synthesis and counteract the effect androgens have on spermatogenesis. Their long term use, however, is undesirable since it can lead to sterility.

The present applicant considers that the use of long term GnRH agonist therapy to desensitise pituitary receptors and hence reduce gonadotroph production with a consequent reduction or elimination of androgens, is an adequate alternative to castration and the use of antiandrogens.

Accordingly, in a fourth aspect, the present invention consists in a method of treating benign prostatic hyperplasia in an animal, the method comprising administering to the animal a formulation comprising about 2–10% (w/w) of at least one GnRH agonist or analogue (on an active basis), about 0.5–2.5% (w/w) lecithin and the balance stearin.

In a preferred embodiment of the method of the fourth aspect, the formulation utilised comprises about 5–10% (w/w) GnRH agonist or analogue (on an active basis), about 0.5–1.5% (w/w) lecithin and about 89–94% (w/w) stearin.

The at least one GnRH agonist or analogue is preferably selected from the group consisting of deslorelin, goserelin, leuprorelin, triptorelin, meterelin, buserelin, histrelin, nafarelin and combinations thereof. It is presently preferred that the GnRH agonist or analogue is deslorelin.

Deslorelin is described in U.S. Pat. No. 4,218,439. Deslorelin has the formula [6-D-tryptophan-9-(N-ethyl-L prolinamide)-10-deglycinamide] or P Glutamine-Histidine-Tryptophan-Serine-Tyrosine-D Tryptophan-Leucine-Arginine-Proline-ethylamide.

In a still further preferred embodiment of the method of the fourth aspect, the formulation utilised is for administration to dogs, cats, other domestic animals, captive wildlife and/or humans.

Again, the excipient(s) of stearin and lecithin is preferably in a non-crystalline form.

Typically, the formulation utilised in the method of the fourth aspect will release the GnRH agonist or analogue, in vitro, into phosphate buffered saline (prepared as described above), at 37° C. at a rate of about 2–80 µg/day for at least 200 days but preferably at least 300 days.

Examples of methods of producing the formulation for administration as implants, particularly to dogs, are provided in PCT/AU96/00379. As is described therein a formulation comprising 94% stearin, 5% deslorelin (on an active basis) and 1% lecithin was evaluated in dogs. This formulation was produced as follows:

Stearin (supplied as free flowing beads of 1 mm or less in diameter made by Vandenberg Foods) and lecithin (supplied as a deep brown viscous syrup from R P Schearer) were hand mixed using a spatula in a small beaker. The deslorelin was then added and thoroughly mixed into the excipients. The mixed material was transferred to the barrel of a ram extruder that has a 1 mm nozzle attached and is equilibrated to 55° C. The ram extrusion pressure is 40 psi. The ram was attached and pressure applied until the product began to extrude. At this point the pressure was backed off and the product allowed to reach 55° C. The product was then extruded—3 g over a 30 second period. The resulting extrudate was allowed to cool and then broken up and re-extruded through a 1 mm nozzle. This step was included to ensure uniformity of content throughout the matrix. The 1 mm nozzle was then replaced with a 2.3 mm diameter nozzle. The same product temperature equilibration procedure was conducted prior to extrusion. The product was then extruded and after cooling the long rods produced could be sectioned into lengths of the required weight.

Whilst this method of production involves extrusions at 55° C., temperatures below this (e.g. 52° C.) which soften the stearin are also suitable.

The rods produced were implanted into male dogs using standard techniques. Results obtained demonstrated that the release of deslorelin from the rods in vitro followed a reproducible path and continued for up to 250 days. In the dogs a continued decline in testicular size was seen for at least 5 months and suppression of plasma testosterone levels for at least 4 months were observed.

In addition, as is also described in PCT/AU96/00379, a formulation comprising 93% stearin, 5% deslorelin (on an active basis) and 2% lecithin was evaluated in dogs. This formulation was produced as follows:

Stearin beads (ADMUL PO 58 from Quest International Australasia Limited) and lecithin (Topcithin 300, Bronson &

Jacobs, Australia) were hand mixed using a spatula in a small beaker. The deslorelin was then added and thoroughly mixed into the excipients. The material was transferred to the barrel of a ram extruder that has a 1 mm nozzle attached and is equilibrated to 55.8° C. The ram extrusion pressure is 40 psi. The ram was then attached and pressure applied until the product began to extrude. At this point the pressure was backed off and the product allowed to reach 55.8° C. The product was then extruded—3 g over a 30 second period. The resulting extrudate was allowed to cool and then broken up before re-extruding the mixed granulation through the 1 mm nozzle at 58.3° C. and into an injectable mould that generates a finished rod product that is 2.3 mm in diameter and approximately 25 mm long. The rods are then sterilised by gamma irradiation.

The rods produced were implanted into male and female dogs (0.5, 1 or 2×120 mg rod containing 6 mg of deslorelin). The results showed that the formulation is able to suppress testosterone levels in dogs for 12 months or more and in bitches for at least 5 months. Accordingly, the formulation of the present invention is able to prevent reproductive function in dogs over an extended period of time.

In further experiments, rods containing goserelin, leuprolide, buserelin or triptorelin were produced in the same manner as described above except that the deslorelin was replaced with the goserelin, leuprolide, buserelin or triptorelin.

BRIEF DESCRIPTION OF THE DRAWINGS

The invention will now be described in more detail with reference to the accompanying drawings, in which:

FIGS. 1–8 show the results of implantation into dogs of rods in accordance with the invention in scrotal circumference monitored over time (Treatments 1–8); and FIGS. 9–14 show the results of monitoring of plasma testosterone levels in the implanted dogs treated in accordance with Treatments 1–6 described in FIGS. 1–6, respectively.

EXAMPLE

Effect of Rod Implants Comprising GnRH Agonists on Scrotal Circumference and Plasma Testosterone Levels Rods in accordance with the invention were implanted into dogs and change in scrotal circumference (which is closely related with testicle size and plasma testosterone levels) monitored over time. The results obtained are shown in the accompanying FIGS. 1 to 8 in which:

| Treatment 1 | Control (0 mg) | (FIG. 1) |
| Treatment 2 | Deslorelin 3 mg | (FIG. 2) |
| Treatment 3 | Deslorelin 6 mg | (FIG. 3) |
| Treatment 4 | Deslorelin 12 mg | (FIG. 4) |
| Treatment 5 | Goserelin 6 mg | (FIG. 5) |
| Treatment 6 | Leuprolide 6 mg | (FIG. 6) |
| Treatment 7 | Buserelin 6 mg | (FIG. 7) |
| Treatment 8 | Triptorelin 6 mg | (FIG. 8) |

The amount (mg) each dog received refers to the amount of the respective GnRH agonist implanted in the dog. Each treatment was tested on five dogs.

Plasma testosterone levels were also monitored in the implanted dogs treated in accordance with Treatments 1 to 6. The results are shown in the accompanying FIGS. 9 to 14.

Histopathological examination conducted on some of the treated dogs at the site of implant revealed that the rods cause minimal or only mild inflammation. Remnants of the implants were found to be encapsulated by a thin layer of fibroblasts.

Dog 1: Treatment 1—implant in place for approx. 14 months.

Remnants of the implant appeared to be "walled off" from the surrounding subcutaneous fatty tissue by a thin capsule of fibroblasts with an inner lining of macrophages that appear to be invading the capsule. There was only a mild multi-focal lymphoplasmacytic inflammation in the connective tissue surrounding the encapsulated implant.

Dog 4: Treatment 3—implant in place for approx. 13 months.

Remnants of the implant were present and appeared as amorphous eosinophilic material in the subcutaneous fatty tissue, walled off by a thin capsule of fibroblasts. There was no significant inflammation associated with the encapsulated implant and the subcutaneous fatty tissue surrounding the implant appeared normal.

Dog 79: Treatment 3—implant in place for approx. 14 months.

Remnants of the implant appeared to be present in the subcutaneous fatty tissue and appeared to be surrounded by a thin capsule of fibroblasts including a few inflammatory cells (macrophages). There was no significant inflammation and the subcutaneous fatty tissue appeared to be normal.

Dog 95: Treatment 2—implant in place for 25 days.

The implant site located in the subcutaneous fatty tissue contained remnants of an amorphous, acellular inert substance surrounded by a layer (3–4 cells thick) which contained a mixture of mononuclear cells. These findings are consistent with a very mild foreign body reaction.

The term "on an active basis" is to be given its usual meaning in the art. That is, it is used to indicate that the % amount (w/w) of peptide agonist or analogue present in a formulation is based on the dry weight of the peptide agonist or analogue.

The terms "comprise", "comprises" and "comprising" as used throughout the specification are intended to refer to the inclusion of a stated component or feature or group of components or features with or without the inclusion of a further component or feature or group of components or features.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A pharmaceutical and/or veterinary solid implant formulation comprising about 2–15% (w/w) of at least one GnRH agonist peptide (on an active basis), about 0.5–3.5% (w/w) lecithin and the balance stearin, wherein said GnRH agonist peptide is other than deslorelin.

2. A formulation according to claim 1, comprising about 5–10% (w/w) of the GnRH agonist peptide (on an active basis), about 0.5–1.5% (w/w) lecithin and about 89–94% (w/w) stearin.

3. A formulation according to claim 2, comprising about 5% (w/w) of the GnRH agonist peptide (on an active basis), 1% (w/w) lecithin and the 94% (w/w) stearin.

4. A formulation according to claim 2, comprising about 5% (w/w) of the GnRH agonist peptide (on an active basis), 2% (w/w) lecithin and 93% (w/w) stearin.

5. A formulation according to claim 1, wherein the lecithin and stearin are in non-crystalline form.

* * * * *